(12) United States Patent
Müller et al.

(10) Patent No.: US 12,151,869 B2
(45) Date of Patent: Nov. 26, 2024

(54) CONTAINER DEVICE HAVING AN OPHTHALMIC INJECTOR HOLDING AN INTRAOCULAR LENS

(71) Applicant: Carl Zeiss Meditec AG, Jena (DE)

(72) Inventors: Marco Müller, Berlin (DE); Andre Wolfstein, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/525,194

(22) Filed: Nov. 30, 2023

(65) Prior Publication Data

US 2024/0109711 A1  Apr. 4, 2024

Related U.S. Application Data

(63) Continuation of application No. PCT/EP2022/069830, filed on Jul. 15, 2022.

(30) Foreign Application Priority Data

Aug. 2, 2021  (DE) ...................... 10 2021 208 333.1

(51) Int. Cl.
*B65D 81/26* (2006.01)
*B65D 77/20* (2006.01)
(Continued)

(52) U.S. Cl.
CPC ........... *B65D 81/264* (2013.01); *B65D 77/20* (2013.01); *B65D 81/22* (2013.01); *B65D 85/38* (2013.01)

(58) Field of Classification Search
CPC ........ A61F 2/16; A61F 2/1662; A61F 2/1664; A61F 2/167; A61F 2/1672; A61F 2/1678;
(Continued)

(56) References Cited

U.S. PATENT DOCUMENTS 5,616,184 A    4/1997   Duncan et al.
2002/0029981 A1  3/2002   Nigam
(Continued)

FOREIGN PATENT DOCUMENTS

AT             12360 U1   4/2012
DE   10 2014 005 719 A1  10/2015
(Continued)

OTHER PUBLICATIONS

International Search Report of the European Patent Office dated Dec. 8, 2022 for international application PCT/EP2022/069830 on which this application is based.

(Continued)

*Primary Examiner* — Bryon P Gehman
(74) *Attorney, Agent, or Firm* — Walter Ottesen, P.A.

(57) ABSTRACT

A container has an ophthalmic injector holding an intraocular lens and a first vessel at least partially filled with a fluid. The intraocular lens is surrounded by the fluid and the first vessel is provided with a lid which closes the first vessel in a fluid-tight manner and which is releasably connected to the first vessel. A second vessel is coupled to the first vessel. A fluid-tight closure is provided between the first vessel and the second vessel, wherein the lid is coupled to the closure by a coupler, and, when the lid is released from the first vessel, the closure is configured, via the coupler, to pass from a closed position to an open position, such that the fluid can flow from the first vessel into the second vessel.

8 Claims, 8 Drawing Sheets

(51) Int. Cl.
   *B65D 81/22* (2006.01)
   *B65D 85/38* (2006.01)
(58) Field of Classification Search
   CPC ........ A61F 2/1682; A61F 2/1691; A61F 9/00;
         A61F 9/007; A61M 5/315; B65D 77/20;
         B65D 81/22; B65D 81/264; B65D 85/38
   USPC .............................................. 206/204–213.1
   See application file for complete search history.

(56) References Cited

U.S. PATENT DOCUMENTS

| | | |
|---|---|---|
| 2007/0000801 A1 | 1/2007 | Mauran et al. |
| 2007/0213816 A1 | 9/2007 | Sarfarazi |
| 2007/0250068 A1 | 10/2007 | Vincent-Aubry |
| 2009/0018548 A1* | 1/2009 | Charles .................. A61F 2/167 606/107 |
| 2009/0057167 A1 | 3/2009 | Rathert |
| 2011/0245840 A1 | 10/2011 | Seyboth et al. |
| 2015/0114855 A1 | 4/2015 | Glick et al. |
| 2017/0042666 A1 | 2/2017 | Maroscheck et al. |
| 2020/0038176 A1 | 2/2020 | Pagnoulle et al. |
| 2022/0354635 A1 | 11/2022 | Dockhorn |

FOREIGN PATENT DOCUMENTS

| | | |
|---|---|---|
| WO | 2010/105678 A1 | 9/2010 |
| WO | 2013/159045 A1 | 10/2013 |
| WO | 2018/015784 A1 | 1/2018 |
| WO | 2021/062568 A1 | 4/2021 |

OTHER PUBLICATIONS

English translation and Written Opinion of the International Searching Authority dated Dec. 8, 2022 for international application PCT/EP2022/069830 on which this application is based.

English translation and International Preliminary Report on Patentability of the International Bureau of WIPO dated Feb. 6, 2024 for international application PCT/EP2022/069830 on which this application is based.

English translation and Office Action of the German Patent Office dated Apr. 14, 2022 for German application No. 10 2021 208 333.1 on which this application is based.

English translatioin and Office Action of the Chinese Patent Office dated Jul. 24, 2024 for corresponding Chinese patent application No. 202280054225.8.

* cited by examiner

CONTAINER DEVICE HAVING AN OPHTHALMIC INJECTOR HOLDING AN INTRAOCULAR LENS

CROSS-REFERENCE TO RELATED APPLICATIONS

This application is a continuation application of international patent application PCT/EP2022/069830, filed Jul. 15, 2022, designating the United States and claiming priority from German application 10 2021 208 333.1, filed Aug. 2, 2021, and the entire content of both applications is incorporated herein by reference.

TECHNICAL FIELD

The disclosure relates to a container device which has an ophthalmic injector having an intraocular lens.

BACKGROUND

Intraocular lenses (IDLs) typically fall into two groups: hydrophobic intraocular lenses, which absorb less than 1 percent water, and hydrophilic intraocular lenses, which absorb more than 1 percent water. Hydrophobic intraocular lenses can be folded at room temperature, their foldability being ensured by their chemical composition and not by the water, which acts as a plasticizer. By contrast, hydrophilic lenses, which typically contain about 25% by weight water, can be folded at room temperature on account of the absorbed water serving as a plasticizer.

It is assumed by those skilled in the art that hydrophilic intraocular lenses have to be soaked in water or physiological saline solution during storage in order to ensure sufficient hydration, which is required for folding at room temperature. Because of this, such intraocular lenses are packaged in such a way that they are located in a fluid in which they can remain for up to five years before their implantation, without changing their optical, mechanical and chemical properties during this time.

Intraocular lenses are typically implanted through an implantation device, commonly referred to by those skilled in the art as an ophthalmic injector, during cataract surgery. The intraocular lens is preferably stored in the injector in a pretensioned state in order to minimize the risk of incorrect operations due to operating errors. The intraocular lens is stored in a humid environment in order to ensure adequate hydration of the intraocular lens.

For this purpose, at least part of the ophthalmic injector, in which the preferably pretensioned intraocular lens is located, is stored in a container filled with fluid. Water or balanced salt solution (BSS) can be used as fluid.

Such systems are described, for example, in US 2007/0250068 A1, WO 2010/105678 A1, WO 2013/159045 A1, US 2011/0245840 A1 and US 2022/0354635 A1.

However, such systems have a number of disadvantages. First, the sterile gloves worn by a user can become wet when removing the injector from the water bath, and this can increase a risk of contamination, since bacteria can be more easily transmitted from wet surfaces. Second, handling an injector is made more difficult with wet hands, which can lead to problems during the operation. Furthermore, the fluid can spill out of the system, which would result in the surgical environment becoming wet.

In this context, reference is made to U.S. Pat. No. 5,616,184 A, US 2009/0057167 A1, US 2002/0029981 A1 and US 2017/0042666 A1.

SUMMARY

It is an object of the disclosure to make available a container device which enables the ophthalmic injector containing the intraocular lens to be removed in a suitable manner from the container filled with fluid, without the fluid escaping from the container device, and with the surroundings of the container device thus remaining dry.

In addition, it is to be achieved that a user poses the lowest possible risk of contamination after he or she has removed the ophthalmic injector from the container device. It is also an object of the disclosure to make available a container device of the type in question which has a higher level of safety if the container device is accidentally knocked over, the aim being to ensure that most of the fluid remains in the container device and that the surgical environment outside of the container device thus remains substantially dry. Furthermore, it is to be achieved that the container device of the type in question can be manufactured in a simple and cost-effective manner and is composed of the fewest possible individual parts.

A container device according to the disclosure has an ophthalmic injector, which has an intraocular lens, and a first container, which is at least partially filled with a fluid, wherein the intraocular lens is surrounded by the fluid, and the first container is provided with a lid which closes the first container in a fluid-tight manner and which is releasably connected to the first container. The container device additionally has a second container, which is coupled to the first container. A fluid-tight closure is provided between the first container and the second container, the lid being coupled to the closure via a coupling device, and, when the lid is released from the first container, the closure is configured, via the coupling device, to pass from a closed position to an open position, such that the fluid can flow from the first container into the second container.

An injector, which contains an intraocular lens, is thus located in the container device. In addition, the container device has a first container, which is at least partially filled with a fluid. The first container is equipped with a lid which closes the first container in a fluid-tight manner and which is releasably connected to the first container. The lid therefore has the effect that the fluid cannot escape from the first container when the lid is closed. However, the lid can be released from the first container, as a result of which the first container is opened.

The intraocular lens is surrounded by the fluid located in the first container. This is essential since hydrophilic intraocular lenses must be maintained in a hydrated state during storage, which ensures that the intraocular lens remains foldable. The injector can therefore be surrounded by the fluid partially, but also in its entirety. Furthermore, the injector can be located partially, but also in its entirety, in the first container.

Furthermore, the container device has a second container, which is coupled to the first container. The first container and the second container are thus connected to each other.

According to the disclosure, a fluid-tight closure is located between the first container and the second container, the lid being connected to the closure via a coupling device. The closure is configured to pass from a closed position to an open position via the coupling device when the lid is released from the first container, such that the fluid can flow from the first container into the second container. When the lid is closed, the fluid is thus located in the first container. The closure between the first container and the second container is closed. As soon as the lid is released, the closure opens via the coupling device, such that the fluid can flow into the second container. There is then no more fluid in the first container.

This ensures that the fluid is transferred from the first container to the second container. The ophthalmic injector, which contains the intraocular lens, can be removed from the first container without the user having to reach into the fluid. Furthermore, a user is at low risk of contamination after removing the ophthalmic injector from the container device according to the disclosure. Even if the container device is accidentally knocked over, this ensures that most of the fluid remains in the container device and that the surrounding area remains substantially dry. By virtue of the small number of components, the container device according to the disclosure can be manufactured simply and cost-effectively.

The fluid can be water or a balanced salt solution (BSS), among other things.

The coupling device can be, among other things, a cord, a ribbon, a string, a rope, or a tensile connection in the form of a wire. The coupling device can also be part of the first container, which is connected to the lid. The fluid-tight closure can also be part of the first container. A wall of the first container, which is a side wall or a bottom wall of the first container, can have a first wall region with a first thickness and a second wall region with a second thickness. The fluid-tight closure can be formed at least partially by part of the wall of the first container, the closure being at least partially delimited by the second wall region. The second thickness is smaller than the first thickness, such that a predetermined breaking point is provided around the closure. When the lid is opened, the tensile force is transferred via the coupling device to the closure, which breaks open at the part of the wall of the first container having the second thickness, such that the closure passes from a closed position to an open position. This makes it possible for the fluid to flow off into the second container.

If the fluid-tight closure is arranged on a side wall, the container device can be made very compact. The bottom wall can then be made so small that there is room on it only for the injector, and no additional surface area for the closure has to be provided on the bottom wall.

According to an embodiment of the disclosure, the fluid-tight closure has a surface area, the surface area of the closure having a size in a range of 50% to 20% of the surface area of a wall of the container device, the wall being a side wall or a bottom wall. The surface area of the closure can also have a size in a range of 20% to 10% of the surface area of a wall of the container device, or a size in a range of 10% to 1% of the surface area of a wall of the container device, or has a size in a range of 1% to 0.2% of the surface area of a wall of the container device. This ensures that if the container device is inadvertently knocked over when the closure is in the open position, some of the fluid remains in the second container or can escape only after a delay. This makes it more sure that, in the event of such accidental knocking over of the container device, the area surrounding the container device remains largely dry. It also ensures that the fluid can flow sufficiently quickly from the first container into the second container.

The fluid-tight closure is preferably configured as a one-way valve. For this purpose, it is advantageously achieved that the fluid can no longer flow back from the second container into the first container. Thus, on account of the one-way valve, the fluid remains completely in the second container. The advantage of this is also that no active activity is required on the part of the user of the container device according to the disclosure in order to enclose the fluid separately from the injector. This further increases the level of safety when handling the container device, since there is a high degree of certainty that no fluid can escape from the second container into an operating environment.

According to an embodiment of the disclosure, there is a first pressure in the first container and a second pressure in the second container. In a preferred embodiment, the second pressure is lower than the first pressure, which means that when the lid is opened, the fluid can flow from the first container into the second container more quickly than if the pressure in both containers were the same. It is thereby possible for the user of the container device to be able to remove the injector from the first container relatively quickly without having to reach into the fluid.

In a further embodiment, at least one wall of the second container, which is a side wall or a bottom wall of the second container, has at least one zone which has a lower spring constant than a region of the wall surrounding this zone. In this way, it is advantageously achieved that when the pressure in the second container increases, the volume of the second container can increase relative to the volume of the first container. The resulting positive effect is that a greater proportion of the fluid can get into the second container, even if the volume of the second container is initially kept as small as possible on account of the space to be saved for transport purposes when the lid is closed.

Preferably, the second container has a fluid-absorbing device. The fluid-absorbing device can include, among other things, a sponge, silica gel, a desiccant, or another water-absorbing agent. In this way, it is advantageously achieved that the fluid can be received in the second container in such a way that it is no longer freely movable. For example, the fluid in the second container is prevented from having a fluctuating fluid level in the event of spatial displacement. This also reduces the risk of the fluid being able to flow out of the second container into its surroundings in the event of considerable spatial movement.

Furthermore, it is possible that the lid closes the second container in a fluid-tight manner and is releasably connected to the second container. The first container is thus located in the second container, as a result of which the container device is advantageously relatively compact.

Preferably, the coupling device is part of the first container, such that there is a one-piece construction of the coupling device with the first container. One end of this coupling device is connected to the closure such that, when a pulling force is applied to the coupling device, the closure, which likewise forms part of the first container, can break open.

BRIEF DESCRIPTION OF DRAWINGS

The invention will now be described with reference to the drawings wherein.

DETAILED DESCRIPTION

Figure 1:
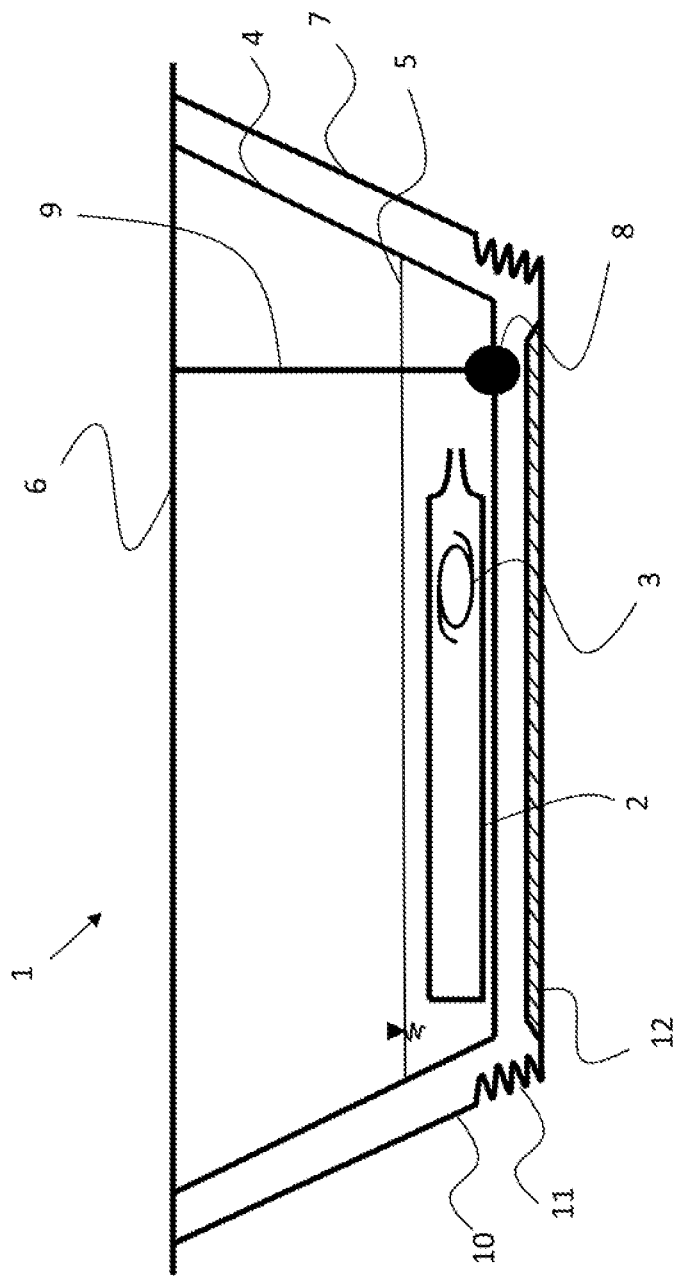
FIG. 1 shows a schematic representation of a cross-sectional view of a container device according to a first embodiment of the disclosure in a closed position.

FIG. 1 shows a schematic representation of a cross-sectional view of a container device 1 according to a first embodiment in a closed position. The container device 1 has an ophthalmic injector 2 in which an intraocular lens 3 is located. The intraocular lens 3 is preferably in a pretensioned state.

The container device 1 also has a first vessel or first container 4, in which the ophthalmic injector 2 is located. The first container 4 is at least partially filled with a fluid 5, the intraocular lens 3 being completely surrounded by the fluid 5. This ensures that the intraocular lens 3 is in a hydrated state during storage. A hydrophilic intraocular lens 3 thus remains easily foldable. It will be seen that the injector 2 can be surrounded by the fluid 5 partially, but also in its entirety.

The first container 4 has a lid 6, which closes the first container 4 in a fluid-tight manner and which is releasably connected to the first container 4. The lid 6 thus ensures that the fluid 5 cannot escape from the first container 4 when the lid 6 is closed. The lid 6 can be at least partially released from the first container 4 by a user, such that the first container 4 is opened at least in a partial region. When the lid 6 is opened in this way, the ophthalmic injector 2 in which the intraocular lens 3 is located can be removed from the first container 4.

The container device 1 has a second vessel or second container 7, which is coupled to the first container 4. The first container 4 is thus connected to the second container 7. In the first embodiment shown in FIG. 1, the first container 4 is located in the second container 7, as a result of which the container device 1 is of relatively compact configuration. In this embodiment, the lid 6 also closes the second container 7 in a fluid-tight manner in addition to the first container 4. Moreover, the lid 6 is likewise releasably connected to the second container 7.

There is a fluid-tight closure 8 between the first container 4 and the second container 7. The fluid-tight closure 8 ensures that the fluid 5 cannot flow from the first container 4 into the second container 7 if the closure 8 is in a closed position.

The second container 7 has at least one wall 10, in particular a side wall, in which there is at least one zone 11 which has a lower spring constant than a region of the wall 10 surrounding this zone 11. The zone 11 is therefore more elastic than the region which surrounds this zone 11. Thus, in the event of a force resulting from increasing pressure within the second container 7 relative to the surrounding region, the zone 11 is able to expand, as a result of which the volume of the second container 7 increases relative to the volume of the first container 4. This has the advantage that a greater proportion of the fluid 5 can flow into the second container 7, although the volume of the second container 7 is kept as small as possible when the lid 6 is closed, so as to save as much space as possible when the container device 1 is being transported. The zone 11 can be configured in the form of a bellows or as a leporello fold. The zone 11 can also be made of a material different than the material that surrounds the region of this zone 11.

In addition, a fluid-absorbing device 12 is located within the second container 7. The fluid-absorbing device 12 can at least partially absorb the fluid 5 as soon as the fluid 5 flows from the first container 4 into the second container 7. The fluid 5 is at least partially stored in the second container 7 via the fluid-absorbing device 12, as a result of which the fluid 5 is at least partially bound and is no longer freely movable in the second container 7. This reduces the amount of fluid 5 that can run out of the second container 7 if the second container 7 is shifted spatially, for example if it is tilted. This reduces the likelihood of the region around the container device 1 becoming wet if the container device 1 is accidentally knocked over.

As already mentioned above, the fluid 5 can flow from the first container 4 into the second container 7. For this purpose, the lid 6 is coupled to the fluid-tight closure 8 via a coupling device 9. As soon as the lid 6 is released from the first container 4, the closure 8 is opened. The closure 8 thus passes from a closed position to an open position upon opening of the lid 6 via the coupling device 9. When the closure 8 is opened, the fluid 5 flows from the first container 4 into the second container 7. This situation can be seen in FIG. 2.

Figure 2:
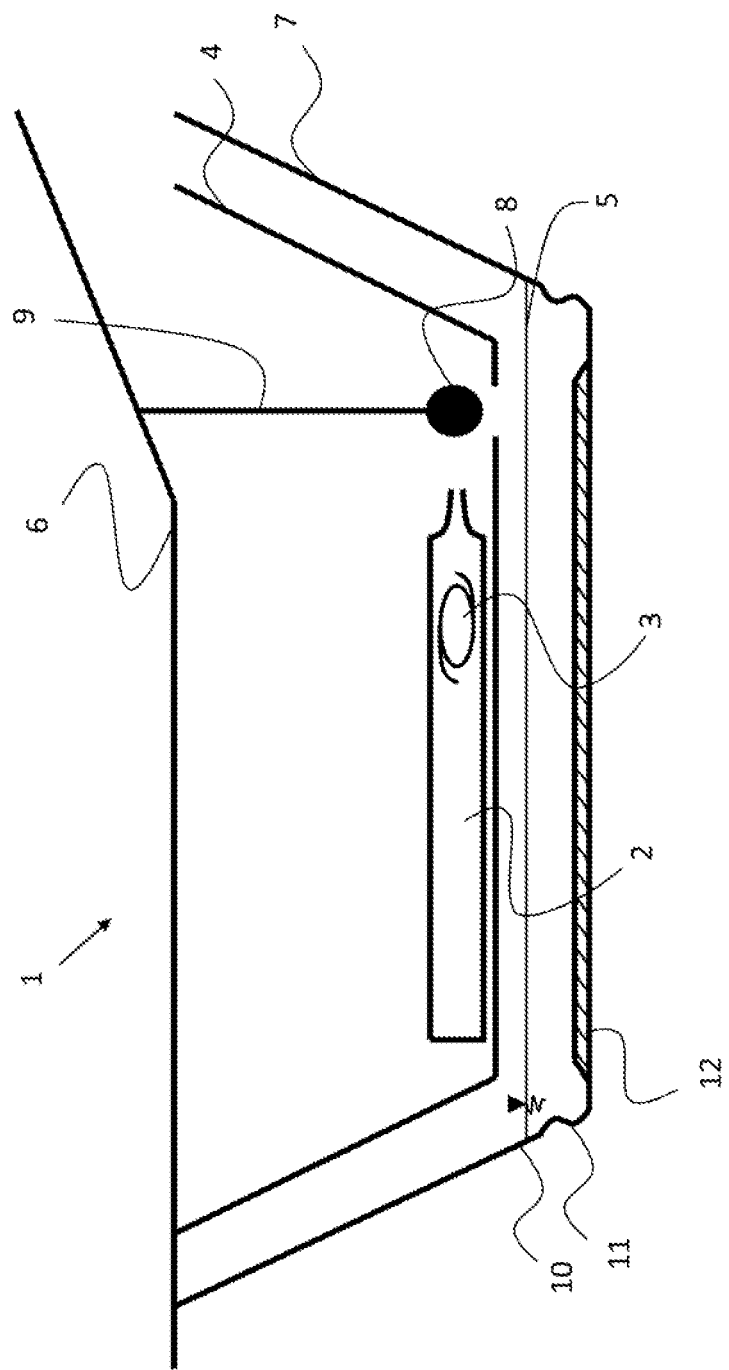
FIG. 2 shows a schematic representation of the cross-sectional view of the container device according to the first embodiment in an open position.

FIG. 2 shows a schematic representation of the cross-sectional view of the container device 1 according to the first embodiment in an open position. By opening of the lid 6, the closure 8 is opened via the coupling device 9 and the fluid 5 flows from the first container 4 into the second container 7, so that there is then no fluid 5 inside the first container 4. In this situation, the ophthalmic injector 2 can be removed from the container device 1 without the fluid 5 coming into contact with the user. The fluid 5 can be at least partially absorbed in the second container 7 by the fluid-absorbing device 12, as a result of which the amount of freely movable fluid 5 is reduced.

In addition, in this embodiment, opening the lid 6 creates a pressure equalization between the first container 4 and the second container 7. Before the lid 6 is opened, the pressure inside the second container 7 is lower than the pressure inside the first container 4. When the lid 6 is opened, the zone 11 located on the wall 10 of the second container 7, and having a lower spring constant than the region of the wall 10 surrounding this zone 11, expands, so that the volume of the second container 7 increases relative to the volume of the first container 4.

Figure 3:
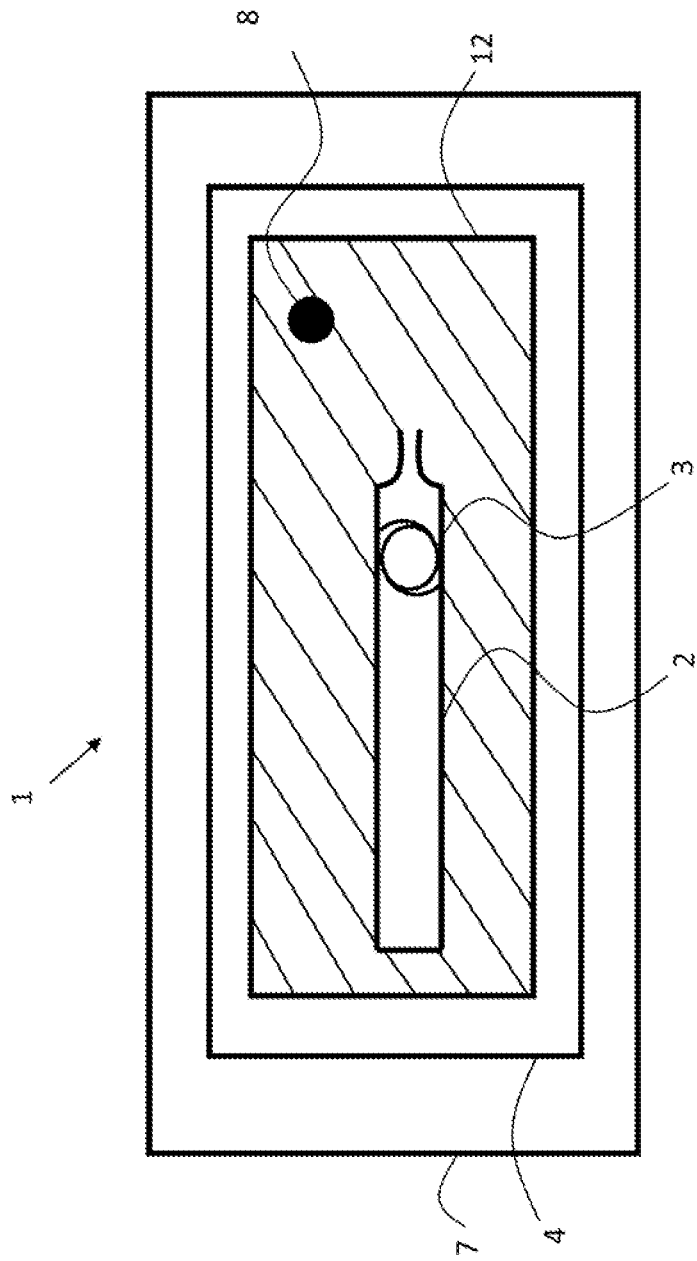
FIG. 3 shows a schematic representation of a plan view of the container device according to the first embodiment.

FIG. 3 shows a schematic representation of a plan view of the container device 1 according to the first embodiment shown in FIG. 1. It will be seen that, in the first embodiment, the first container 4 is located in the second container 7, as a result of which the container device 1 is of relatively compact configuration. The injector 2 is preferably fixed inside the first container 4, which ensures that the container device 1 and thus the intraocular lens 3 are transported safely. When the lid 6 is opened, that is, when the closure 8 is in the open position, the intraocular lens 3 is no longer surrounded by the fluid 5, and the injector 2 can be removed from the container device 1 without the user having to reach into the fluid 5. In addition, the fluid-absorbing device 12 is shown in the second container 7. It is also shown that the base area of the fluid-tight closure 8 has a size that is approximately 0.4% of the base area of the container device 1.

Figure 4:
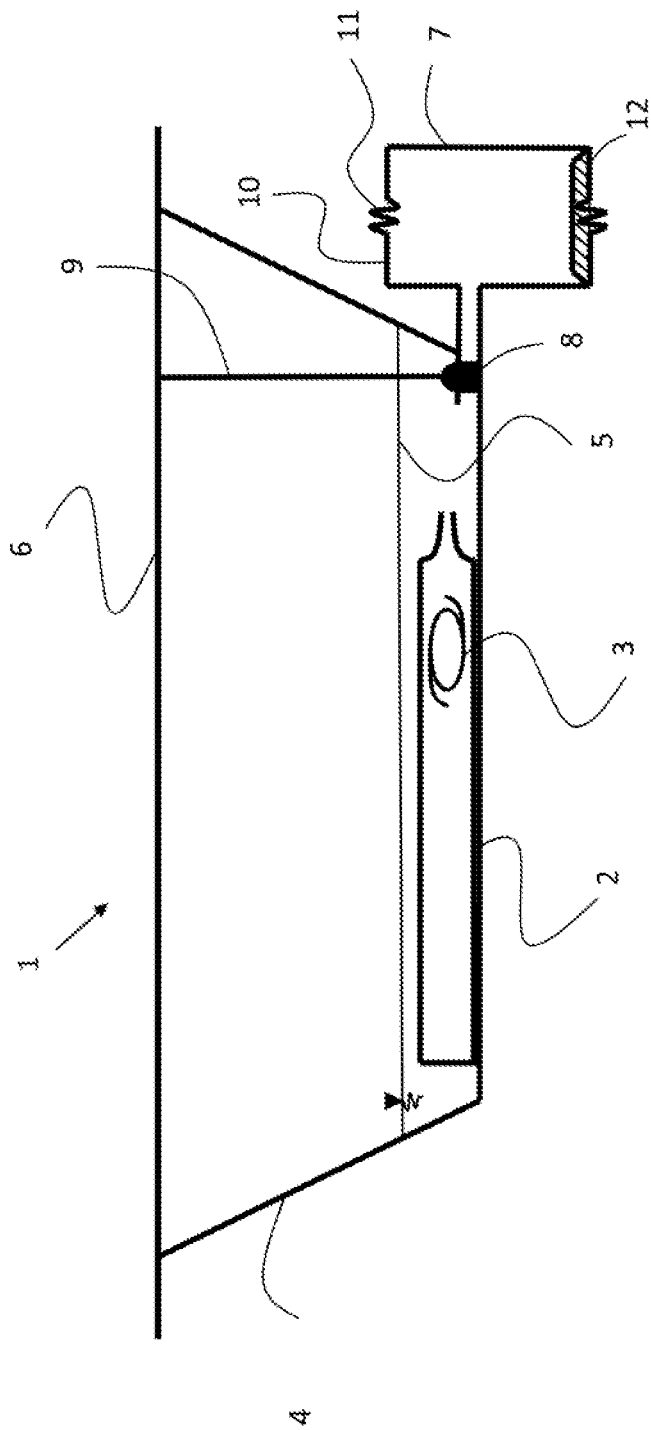
FIG. 4 shows a schematic representation of a cross-sectional view of the container device according to a second embodiment of the disclosure in a closed position.

FIG. 4 shows a schematic representation of a cross-sectional view of the container device 1 according to a second embodiment in a closed position. Although the container device 1 also has a first container 4 and a second container 7 which are coupled to each other, that is, connected to each other, the first container 4 in the second embodiment is not located in the second container 7, unlike in the first embodiment. In this embodiment, the lid 6 only closes the first container 4. In contrast to the first embodiment, the lid 6 does not close the second container 7, and it is not releasably connected to the second container 7 either.

The ophthalmic injector 2, which contains the intraocular lens 3 and is surrounded by the fluid 5, is located in the first container 4. In the closed position, in which the fluid-tight closure 8 connected to the lid 6 is configured such that the fluid 5 cannot flow from the first container 4 into the second container 7, different pressures prevail in the first container 4 and in the second container 7. Put more precisely, the pressure in the first container 4 is higher than in the second container 7, so that by opening of the lid 6, as a result of which the closure 8 passes from the closed position to the open position via the coupling device 9, the fluid 5 arrives more quickly in the second container 7. This open position is shown in FIG. 5.

Figure 5:
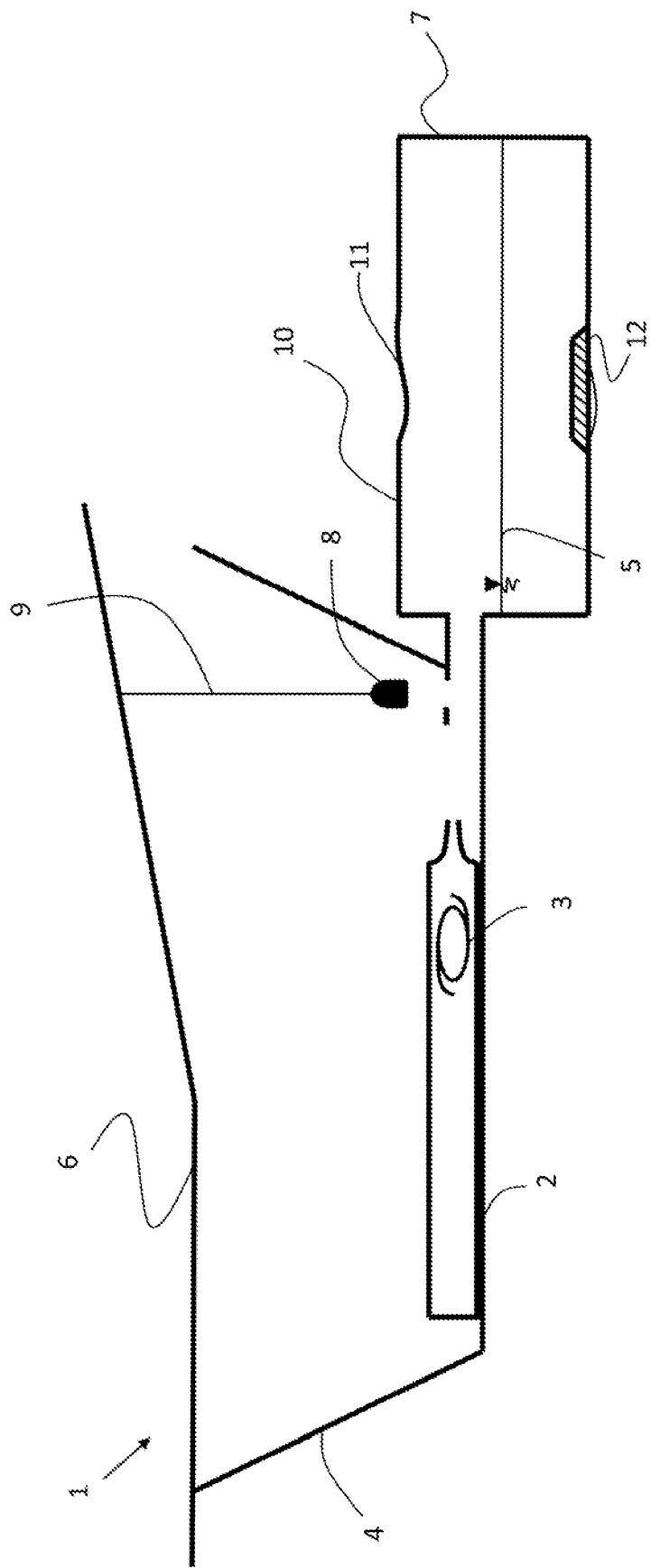
FIG. 5 shows a schematic representation of the cross-sectional view of the container device according to the second embodiment in an open position.

FIG. 5 shows a schematic representation of the cross-sectional view of the container device 1 according to the second embodiment in the open position. By opening of the lid 6, a pressure equalization takes place between the first container 4 and the second container 7, as a result of which the zone 11 of the wall 10, having a lower spring constant than a region of the wall 10 surrounding this zone 11, expands and the volume of the second container 7 increases. The fluid 5 flows into the second container 7 and is at least partially absorbed by the fluid-absorbing device 12.

Figure 6:
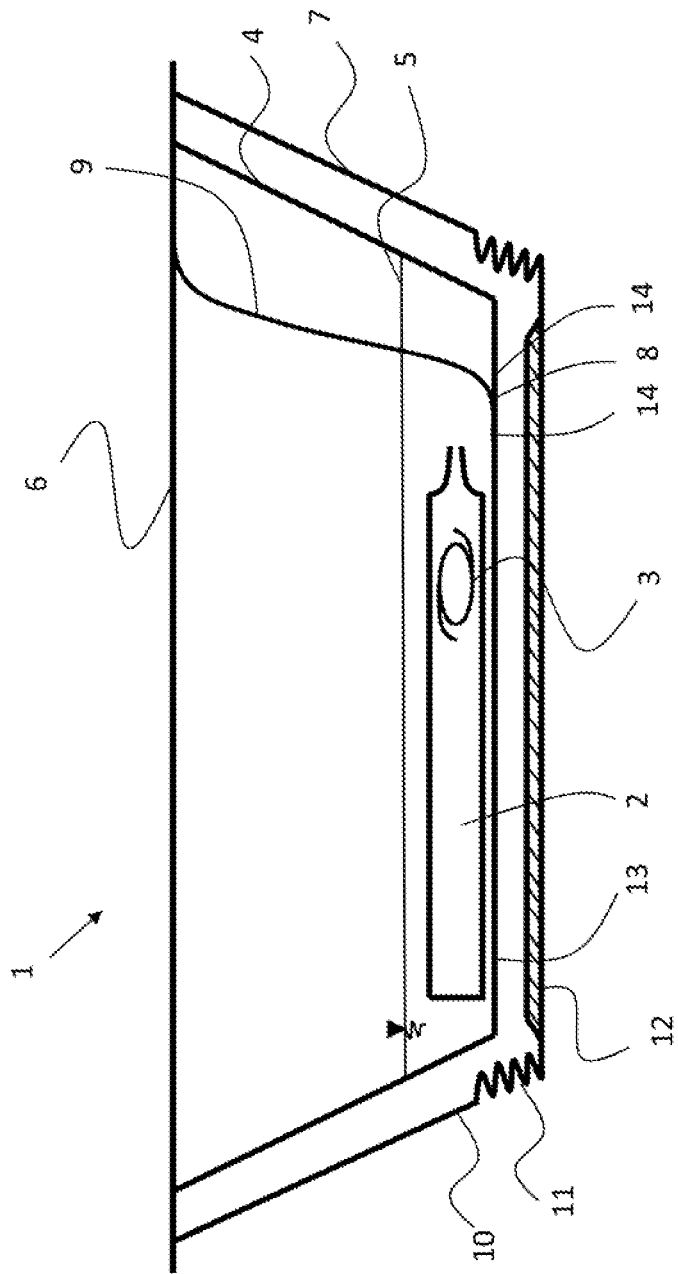
FIG. 6 shows a schematic representation of a cross-sectional view of the container device according to a third embodiment in a closed position.
Figure 7:
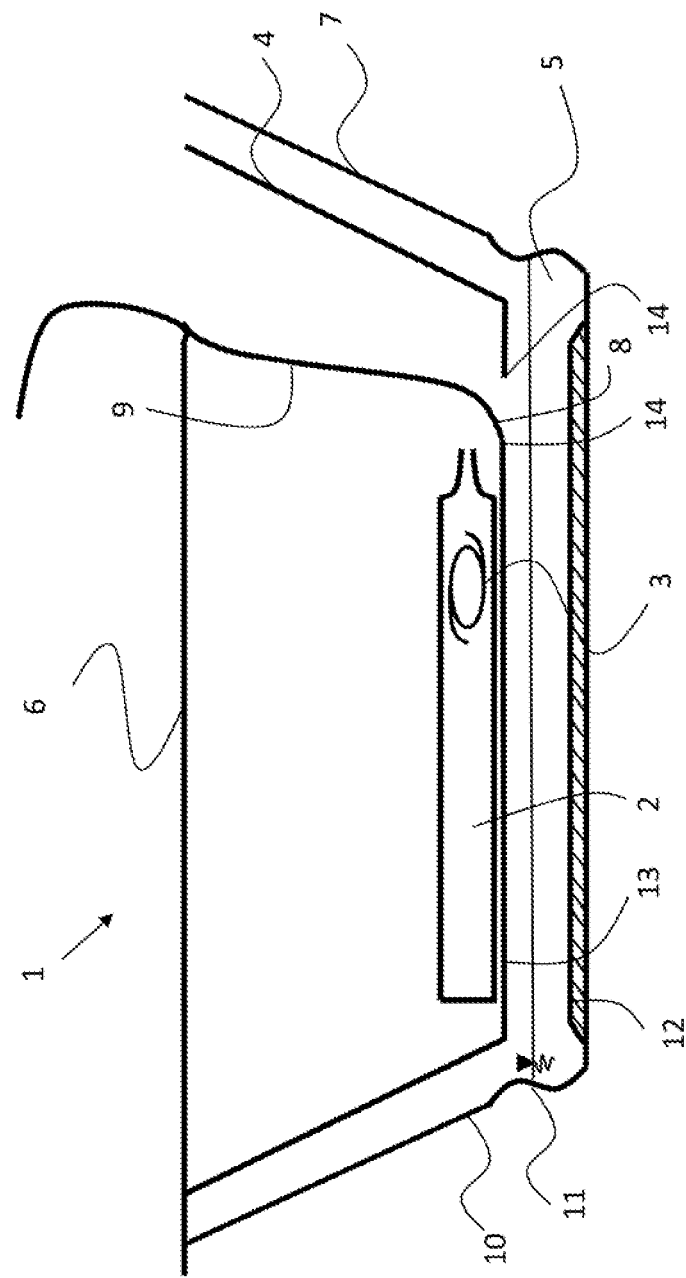
FIG. 7 shows a schematic representation of a cross-sectional view of the container device according to the third embodiment in an open position; and, FIG. 8 shows a schematic representation of a plan view of the first container with a first wall region and a second wall region.
Figure 8:
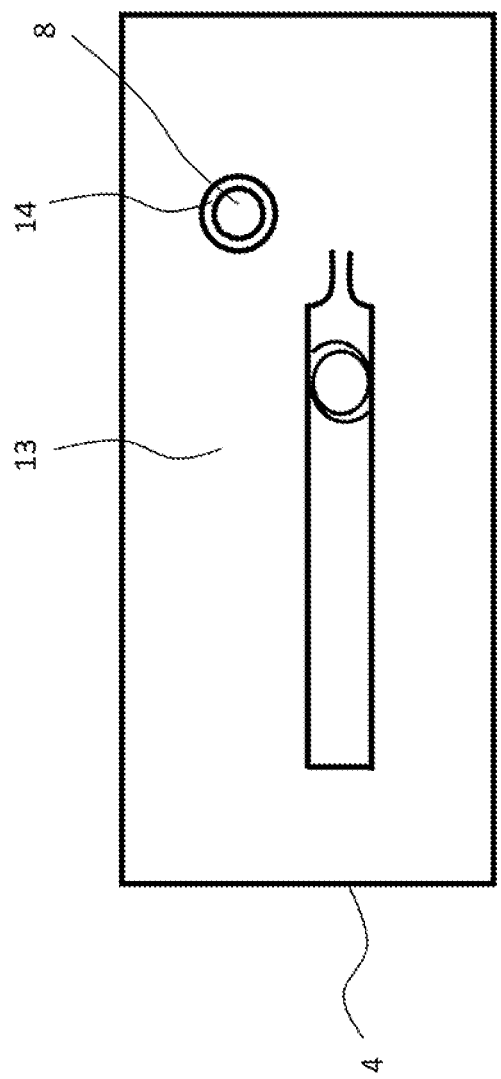

FIG. 6 shows a schematic representation of a cross-sectional view of the container device 1 according to a third embodiment in a closed position. In the third embodiment, the coupling device 9 is a part of the first container 4 that is connected to the lid 6. The fluid-tight closure 8 is also part of the first container 4. A wall of the first container 4, which is a bottom wall here, has a first wall region 13 with a first thickness and a second wall region 14 with a second thickness. In this embodiment, the fluid-tight closure 8 is formed at least partially by part of the bottom wall of the first container 4, the closure 8 being at least partially delimited by the second wall region 14. The second thickness is smaller than the first thickness, as a result of which the closure 8 has a predetermined breaking point. The second wall region 14 can be configured as a ring segment, as a circumferential circular ring, see FIG. 8, or as a circular area. If the second wall region 14 is configured as a circular area, this circular area is the closure 8. When the lid 6 is opened, the tensile force is transferred via the coupling device 9 to the closure 8, which breaks open at the second wall region 14 of the first container 4 having the second thickness, such that the closure 8 passes from a closed position to an open position. This open position is shown in FIG. 7. After breaking open at the predetermined breaking point, the closure 8 can no longer return to its closed position. The container device 1 is thus intended for single use only.

FIG. 7 shows a schematic representation of the cross-sectional view of the container device 1 according to the third embodiment in the open position. By opening of the lid 6, the tensile force is transferred to the fluid-tight closure 8 via the coupling device 9. As a result, the closure 8 breaks open at the second wall region 14 of the first container 4 having the second thickness, such that the closure 8 passes from a closed position to an open position. This ensures that the fluid 5 can flow from the first container 4 into the second container 7 so that there is then no fluid 5 inside the first container 4. When the fluid 5 is received in the second container 7, the ophthalmic injector 2 can be removed from the first container 4 without the user coming into contact with the fluid 5. The fluid 5 can be at least partially absorbed in the second container 7 by the fluid-absorbing device 12, as a result of which the amount of freely movable fluid 5 is reduced.

Preferably, opening the lid 6 creates a pressure equalization between the first container 4 and the second container 7. Before the lid 6 is opened, the pressure inside the second container 7 is lower than the pressure inside the first container 4. If the lid 6 is then opened, the fluid 5 can flow quickly and reliably into the second container 7. On the wall 10 of the second container 7, a zone 11 is preferably provided which has a lower spring constant than the region of the wall 10 surrounding this zone 11, such that the volume of the second container 7 increases relative to the volume of the first container 4 when the fluid 5 flows from the first container 4 into the second container 7.

It is understood that the foregoing description is that of the preferred embodiments of the invention and that various changes and modifications may be made thereto without departing from the spirit and scope of the invention as defined in the appended claims.

LIST OF REFERENCE SIGNS 1 container device
2 ophthalmic injector
3 intraocular lens
4 first vessel or first container
5 fluid
6 lid
7 second vessel or second container
8 fluid-tight closure
9 coupling device
10 wall
11 zone
12 fluid-absorbing device
13 first wall region of the first container
14 second wall region of the first container

The invention claimed is:

1. A container comprising:
an ophthalmic injector holding an intraocular lens;
a first vessel at least partially filled with a fluid surrounding said intraocular lens;
a lid closing off said first vessel in a fluid-tight manner and being releasably connected to said first vessel;
a second vessel coupled to said first vessel;
a fluid-tight closure provided between said first vessel and said second vessel and being movable from a closed position to an open position; and,
a coupler coupling said lid to said closure so as to cause said closure to move from said closed position to said open position in response to said lid being released from said first vessel whereupon said fluid flows from said first vessel into said second vessel.

2. The container of claim 1, wherein said container has a wall defining a surface area and said closure has a surface area having a size lying in a range of: 50% to 20% of said surface area of said wall of said container; or, 20% to 10% of said surface area of said wall of said container; or, 10% to 1% of said surface area of said wall of said container; or, 1% to 0.2% of said surface area of said wall of said container.

3. The container of claim 1, wherein said closure is a one-way valve.

4. The container of claim 1, wherein said first vessel has a first pressure therein and said second vessel has a second pressure therein lower than said first pressure.

5. The container of claim 1, wherein at least one wall of said second vessel has at least one zone having a spring constant lower than a region of said at least one wall surrounding said at least one zone.

6. The container of claim 1, wherein said second vessel has a fluid absorber disposed therein.

7. The container of claim 1, wherein said lid is configured to also close said second vessel in a fluid-tight manner and is releasably connected to said second vessel.

8. The container of claim 1, wherein said coupler is part of said first vessel.

* * * * *